United States Patent [19]
Loosmore et al.

[11] Patent Number: 5,643,753
[45] Date of Patent: *Jul. 1, 1997

[54] USE OF AUTOLOGOUS PROMOTERS TO EXPRESS GENE PRODUCTS IN BORDETELLA

[75] Inventors: Sheena Loosmore, Aurora; Gavin Zealey, Thornhill; Reza Khayyam Yacoob, Mississauga; Michel Klein, Willowdale, all of Canada

[73] Assignee: Connaught Laboratories Limited, Ontario

[*] Notice: The portion of the term of this patent subsequent to Jul. 9, 2012, has been disclaimed.

[21] Appl. No.: 4,301

[22] Filed: Jan. 14, 1993

Related U.S. Application Data

[63] Continuation-in-part of Ser. No. 687,231, Apr. 18, 1991, abandoned.

[30] Foreign Application Priority Data

Apr. 18, 1990 [GB] United Kingdom ................. 9008746

[51] Int. Cl.$^6$ ................. C12N 15/64; C12N 15/31; C12N 1/21; A61K 39/10
[52] U.S. Cl. ................. 435/69.3; 435/91.1; 435/91.4; 435/91.41; 435/172.3; 435/252.3; 435/320.1; 424/93.4; 424/235.1; 424/240.1; 424/253.1; 424/254.1; 536/23.7; 935/10; 935/12; 935/29; 935/41; 935/56; 935/72
[58] Field of Search ................. 435/69.3, 91, 172.3, 435/252.3, 320.1, 91.1, 91.4, 91.41; 424/93 A, 240.1, 253.1, 254.1, 235.1, 93.4; 935/10, 12, 29, 41, 56, 60, 72; 536/23.7

[56] References Cited

U.S. PATENT DOCUMENTS 5,085,862 2/1992 Klein et al. ................. 424/197.11

OTHER PUBLICATIONS

Sambrook et al. Molecular Cloning: A Laboratory Manual 2nd Edition. Cold Spring Harbour Laboratory CSH(NY) 1989, Chapter 16 & 17.
Zealey et al. Fems Microbiology Letters 56:123–126 1988.
Makoff et al, Bio/Technology 1990, 8:1030–1033.
Nicosia et al, Infec. Immun. 1987; 55:963–967.
Burnette et al, Bio/Technology 1988; 6:699–706.
Romanos et al, Vaccine. vol. 9, Dec. 1991, pp. 901–906.
Burnette, Biotechnology, 1990, 8:1002.
Burnette 1991, Vaccine Research, vol. 1, eds. W. Koff et al.
Nicosia et al., Proc. Natl. Acad. Sci., U.S.A.; 83, 4631, (1986);.
Loosmore et al., Nucl. Acids Res., 17, 8365, (1989);.
Relman et al., Proc. Natl. Acad. Sci., U.S.A., 86, 2637, (1989);.
Charles et al., Proc. Natl. Acad. Sci., U.S.A., 86, 3354, (1989);.
Sanger et al., Proc. Natl. Acad. Sci. U.S.A., 74, 5463, (1977);.
Zealey et al., Bio/Technology, 8, 1025, (1990);.
Stibitz et al., Gene, 50, 133, (1986);.
Yacoob and Zealey, Nucl. Acids Res. 16 1639, (1988);.
Imaizumi et al., Infect. Immun. 41, 1138, (1983);.
Loosmore et al., Infect. and Immun. 58, 3653 (1990);.
Zealey et al., Appl. Environ. Microbiol. 58, 208 (1992).

*Primary Examiner*—Anthony C. Caputa
*Attorney, Agent, or Firm*—Sim & McBurney

[57] ABSTRACT

Autologous promoters are used to effect expression of gene products in Bordetella strains. Hybrid Bordetella genes are constructed comprising a Bordetella gene, particularly one encoding a Bordetella antigen, fused at an ATG codon to a native but autologous Bordetella promoter or other Bordetella strain. Genes and promoters from *B. pertussis* are preferred. *B. pertussis*, containing the hybrid gene by insertion into the chromosome of the organism by homologous recombination at specific loci, effects expression of the protein for which the Bordetella gene codes at a production rate different from that achieved for the homologous gene. Specific strains and plasmids are described.

14 Claims, 13 Drawing Sheets

Figure 1. Map of the vector used to integrate the hybrid FHAp/TOX operon at the TOX locus

```
                        FHA              TOX
Hinf I                                            Ava I
   | ATTCTGCCGATTACT TCACTTCGCTGGTCGGAATATGCGT TGCAC |
   | GACGGCTAATGAAGTGAAGCGACCAGCCTTATACGCAACGTGAGCC |
```

Plasmid map: S-3680-10 with sites EcoRI, BglII, BglII/SmaI, AvaI/HinfI, EcoRI, SmaI, SalI; regions 3'TOX, TOX, FHAp, 5'TOX, Amp^r.

Figure 2. Map of the vector used to integrate the hybrid FHAp/TOX operon at the FHA locus
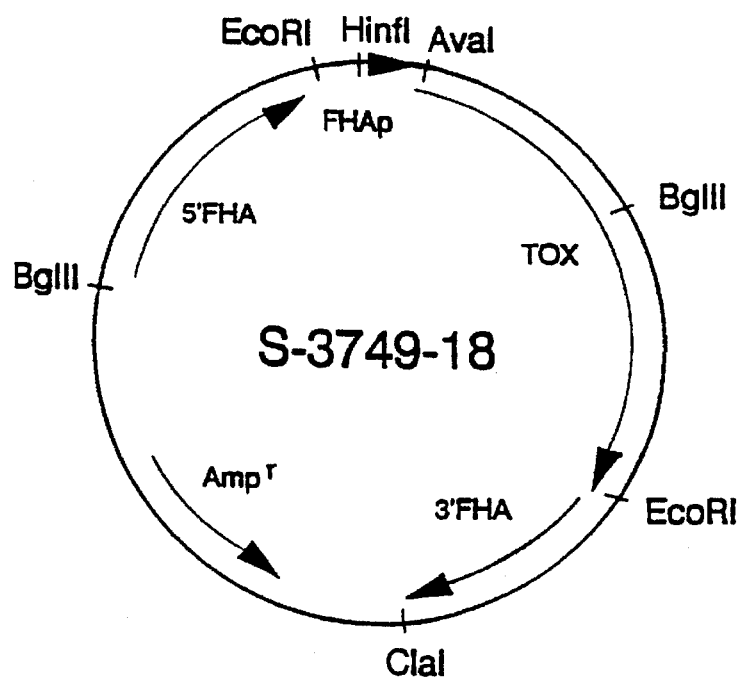

BORDATELLA PERTUSSIS 10536

BORDATELLA PERTUSSIS 390-59

BORDATELLA PERTUSSIS 590-11

PT (mg / L)

Figure 4. Map of the vector used to integrate the the hybrid TOXp/FHA gene at the FHA locus Nco I CATGGTGTGA TCCGT AAAATAGGCA CCATCA AAACG CAGAG GGGAA
CACACT AGGCA TTTTA TCCGT GGTAGT TTTGC GTCTC CCCTT TOX        FHA                                                          Sph I GACGG GATGAAC ACGAACCTGT ACAGG CTGGT CTTCA GCCAT GTTCG CGGCATG
CTGCC CTACTTG TGCTT GGACATGTCC GACCA GAAGTCGGTA CAAGC GCC Plasmid map S-3838-9 with features: EcoRI, KpnI, NcoI, SphI, BamHI, TOXp, 5'FHA, BglII, FHA, BamHI, BglII, Amp^r, ClaI, 3'FHA, EcoRI, BamHI

BORDATELLA PERTUSSIS 10536

BORDATELLA PERTUSSIS 890-49

FHA (mg / L)

Figure 6A. Sequences of the linking oligonucleotides used to construct the FHAp/PRN (A) hybrid gene and map of the integrating vector.
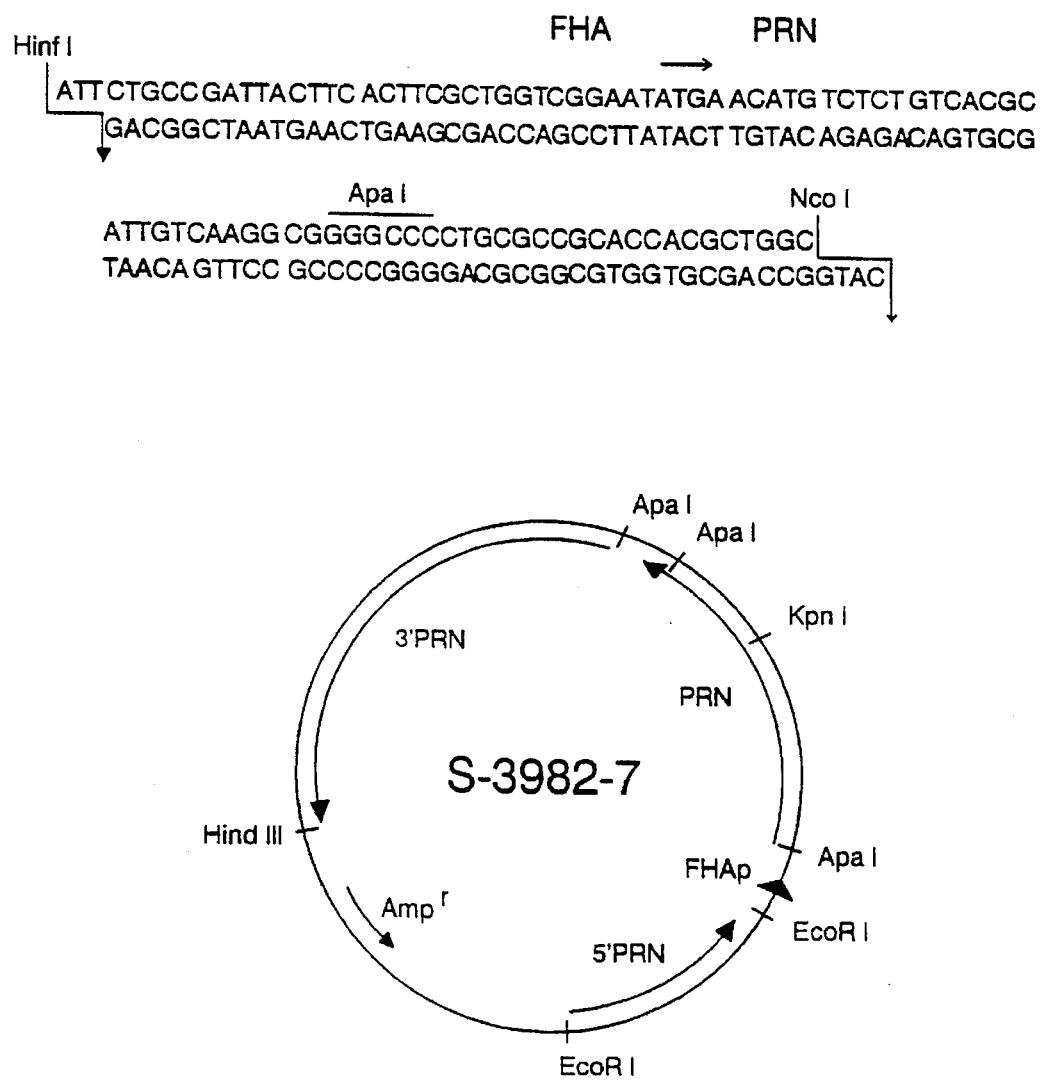

Figure 6B. Sequences of the linking oligonucleotides used to construct the FHAp/PRN hybrid gene and map of the integrating vector
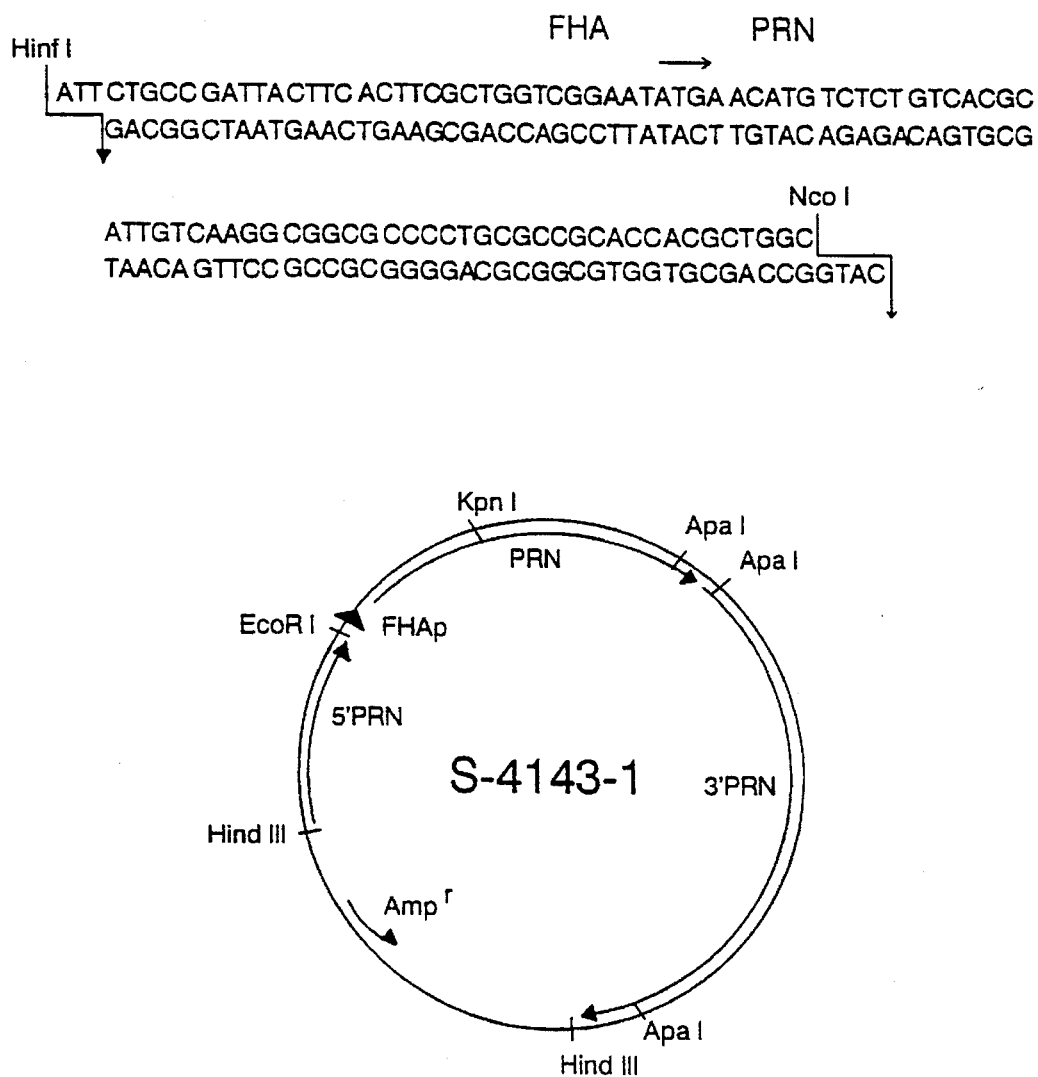

Figure 6C. Sequences of the linking oligonucleotides used to construct the TOXp/PRN (A) hybrid gene and maps of the integrating vectors containing the TOXp/PRN (A) and TOXp/PRN hybrid genes, respectively.

Kpn I

CGGTCACCGTCCGGACCGTGCTGACCCCCCTGCCATGGTGTGATCCGTAAAATAGGCACCATCAAAACGC
CATGGCCAGTGGCAGGCCTGGCACGACTGGGGGGACGGTACCACACTAGGCATTTTATCCGTGG TAGTTTTGCG

TOXp → PRN Apa I

AGAGGGGAAGACGGGATGAACATGTCTCTG TCACGCATTG TCAAGGCGGGGCC
TCTCCCC TTCTGCCCTACTTG TACAGAGACAGT GCGTAACAGTT CCGCC

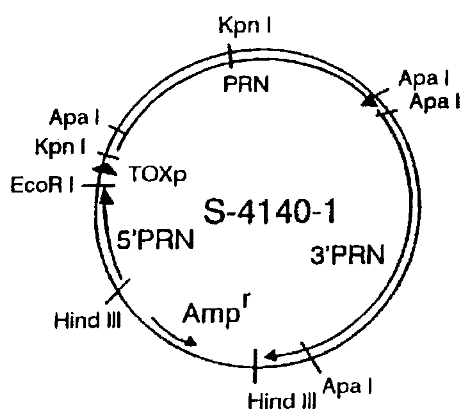

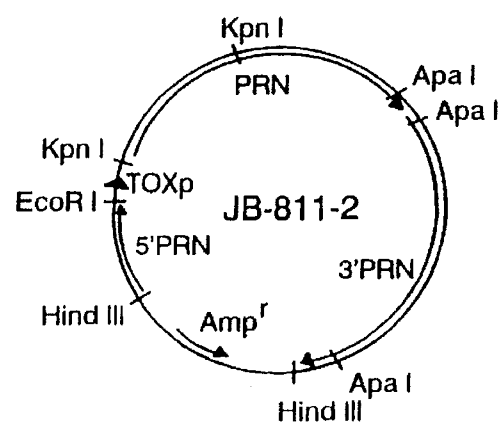

Bordetella pertussis 10536

FIG.7A.

Bordetella pertussis 1290-4

FIG.7B.

Bordetella pertussis 591-473

FIG.7C.

69 kDa (mg/L)
●———

FIG. 8A. Southern analysis of recombinant Bordetella pertussis strain 390-59 containing the FHAp/TOX operon at the TOX locus

FIG. 9A. Southern analysis of recombinant Bordetella pertussis strain 890-49 containing the TOXp/FHA gene at the FHA locus FIG.10A. Southern blot analysis of recombinant Bordetella pertussis strains 1290-4 and 591-473 containing the FHAp/PRN gene at the PRN locus

FIG.11A. Southern blot analysis of recombinant Bordetella pertussis strains 192-35 and 192-10 containing the TOXp/PRN gene at the PRN locus

USE OF AUTOLOGOUS PROMOTERS TO EXPRESS GENE PRODUCTS IN BORDETELLA

REFERENCE TO RELATED APPLICATION

This application is a continuation-in-part of U.S. patent application Ser. No. 07/687,231 filed Apr. 18, 1991, abandoned.

FIELD OF INVENTION

The present invention relates to a novel approach to vary the production of gene products, particularly protein antigens, particularly in species of Bordetella, by changing the promoters of the genes coding for the respective proteins and altering their level of expression.

BACKGROUND TO THE INVENTION

The bacterial species Bordetella comprises *B. pertussis, B. parapertussis, B. bronchiseptica*, and *B. avium*. The first two microorganisms are human pathogens, while the latter two are generally restricted to non-human hosts. *B. pertussis* and *B. parapertussis* cause the disease whooping cough with the former generating more severe symptoms. The disease, or vaccination against the disease (using an inactivated whole-cell vaccine), elicits antibodies against several antigens, typically pertussis toxin (PT), filamentous haemagglutinin (FHA), agglutinogens or fimbriae and the 69 kDa outer membrane protein or pertactin. These proteins represent the major immunogens that may be included, individually or in combination, in any vaccine used to protect against the disease, whether it be the inactivated whole-cell vaccine or a defined component vaccine. Therefore, the efficient expression of these antigens from the vaccine strain is crucial.

During the production of vaccine antigens by fermentation, it has been observed that FHA is secreted at approximately 7 and 10 times the molar level of pertactin and PT, respectively. While protein structural complexity and secretion efficiencies may be important factors influencing antigen yields, the level of expression of *B. pertussis* antigen genes also may be influenced by the relative strength and the regulation of their respective promoters. Thus, it may be possible to optimize antigen production by substituting autologous promoters, which may either increase or decrease the yield of selected antigens. The resulting *B. pertussis* strains would be more economical and better immunogens to use directly in whole-cell vaccines. In addition, promoter interchange also may represent a means to enhance fermentation and downstream processing efficiencies for component vaccines by altering the kinetics of production and yields of specific antigens.

Along with other genes, the pertussis toxin operon (TOX), the filamentous haemagglutinin operon (FHA), and the pertactin gene (PRN) are all positively regulated by the Bordetella virulence regulating gene (Bvg), formerly known as VIR. The nucleotide sequences of the TOX, FHA, and PRN structural genes and their promoters have been established and the corresponding protein sequences derived (see below). For the TOX operon, the Bvg responsive region of the promoter has been mapped to a position −170 bp from the start of transcription. The corresponding regulatory regions of the other genes have not yet been determined.

The use of killed whole-cell pertussis vaccines has resulted in a massive reduction in the incidence of whooping cough since their introduction in the 1950s. These vaccine preparations are efficacious but have been known for many years to be reactogenic and to be associated with local and systemic responses in vaccinees. There has thus been a great deal of effort to develop defined acellular pertussis vaccines containing highly purified, well-characterized and non-reactogenic antigens. Such acellular vaccines are used for immunization in Japan and are at various stages of clinical assessment in other countries. Defined pertussis vaccines consist of several combinations of the *B. pertussis*-specific antigens pertussis toxin (PT), filamentous hemagglutinin (FHA), the 69 kDa outer membrane protein (pertactin) and fimbrial agglutinogens. Replacing whole-cell whooping cough vaccines with the defined acellular preparations has resulted in a substantial increase in the complexity and cost of vaccine manufacture. A major portion of these increased costs is due to the relatively low levels of PT and pertactin produced by *B. pertussis* strains, even when grown under optimized fermentation conditions. Increasing the level of antigen production by *B. pertussis* may be achieved by replacing the natural promoter for a gene encoding an antigen by another promoter as described in the present invention.

SUMMARY OF THE INVENTION

In accordance with the present invention, there is provided a novel method to alter protein expression in Bordetella species by substituting the promoter of one gene of a Bordetella species by that of another gene of a Bordetella species. It is possible to increase or decrease protein expression using this strategy as well as achieving sychronicity or asynchronicity of antigen production.

Accordingly, in one aspect, the present invention provides a hybrid Bordetella gene, comprising a Bordetella gene fused at an ATG start codon to an autologous Bordetella promoter. The Bordetella gene usually encodes an antigen.

Preferably, specific combinations of Bordetella genes and promoters are provided, including the TOX promoter in combination with the FHA or PRN genes; the FHA promoter in combination with the TOX or PRN genes; and the PRN promoter in combination with the TOX or FHA genes. In a particularly preferred embodiment, the Bordetella genes and promoters are those from *Bordetella pertussis*.

The present invention further provides strains of Bordetella, particularly *Bordetella pertussis*, which contain the hybrid genes or multiples of such hybrid genes and which are capable of expression of a gene product of the Bordetella gene or genes. Such strains produce, upon culture, the gene product at a yield of production which is altered from the yield of production achieved by the same Bordetella strain containing a homologous gene comprising a Bordetella gene fused at an ATG start codon to its own native Bordetella promoter.

Specific new *B. pertussis* strains are described in the disclosure which follows, in particular those identified as *B. pertussis* strains Nos. 1290-4, 390-59, 590-473, 192-35, 192-10, 390-59, 590-11 and 890-49. In addition, *B. pertussis* strains from which at least one of the FHA gene and the PRN gene have been removed, particularly strain Nos. 390-101 and 1090-108-3, form other aspects of the invention. The invention further includes the plasmids useful in effecting transformation of the Bordetella, strain particularly *B. pertussis* strains.

The gene products, usually the antigenic proteins, produced by culturing the Bordetella strain containing the hybrid gene generally are useful in vaccines against the disease of whooping cough (pertussis).

An aspect of the invention allows for the easier downstream separation of the resulting proteins, which makes the production of a component vaccine more economical. A further aspect of the invention allows for the preparation of a whole-cell pertussis vaccine in which, because of improved gene expression, antigenic proteins are distributed differently.

The technique described herein for expression of proteins from transformed strains of B. pertussis may be employed with other strains of Bordetella, such as B. parapertussis, B. bronchiseptica and B. avium. The technique also broadly is applicable to hybrid genes formed from any Bordetella gene and any native but autologous Bordetella promoter to effect expression of the desired gene product from a Bordetella strain containing the hybrid gene.

Accordingly, in yet another aspect of the present invention, there is provided a method of expression of a gene product from a Bordetella strain, which comprises forming a hybrid gene comprising a Bordetella gene fused at an ATG start codon to an autologous Bordetella promoter, introducing the hybrid gene into a Bordetella strain to form a transformed Bordetella strain, and culturing the transformed Bordetella strain to effect expression of a gene product encoded by the hybrid gene.

The disclsoure which follows specifically describes the invention with respect to hybrid genes containing promoters and genes of *Bordetella pertussis*, to *Bordetella pertussis* strains containing such hybrid genes, and to gene products of such strains. However, as will be apparent from the above discussion, the invention is broadly applicable to hybrid genes, strains and gene products of other Bordetella species, such as *B. parapertussis, B. brochiseptica* and *B. Avium*.

BRIEF DESCRIPTION OF DRAWINGS

FIG. 1 shows the sequence (SEQ ID: NO 1) of the oligonucleotides used to link the FHA promoter and TOX structural gene sequences, the arrow indicating the location of the ATG start codon of the S1 gene. The plasmid S-3680-10 contains the hybrid operon sandwiched between the flanking regions of TOX and was used for introduction into a TOX deleted strain of *B.pertussis*;

FIG. 2 shows the plasmid S-3749-18 which contains the hybrid FHAp/TOX operon sandwiched between the flanking regions of FHA, used for introduction into an FHA deleted strain of *B. pertussis*;

FIG. 4 shows the sequence (SEQ ID NO: 2) of the oligonucleotide used to link the TOX promoter and FHA structural gene, the arrow indicating the ATG codon of the FHA structural gene. The plasmid S-3838-9 contains the hybrid operon sandwiched between the FHA flanking regions for delivery to the FHA locus of an FHA deleted strain;

FIG. 6A shows the sequence (SEQ ID NO: 3) of the oligonucleotides used to link the FHA promoter and PRN structural gene through a DNA fragment coding for an altered pertactin signal sequence, the arrow indicating the ATG codon of the pertactin gene. The Apa I site which changes a single amino acid (Ala$^{12}$→Gly) in the signal sequence also is indicated. The pUC-based plasmid S-3982-7 contains the FHAp/PRN (A) hybrid gene between the pertactin flanking regions for delivery to the PRN locus of a PRN deleted strain;

FIG. 6B shows the sequence (SEQ ID NO: 4) of the oligonucleotides used to link the FHA promoter and PRN structural gene through the authentic pertactin signal sequence, the arrow indicating the ATG start codon of the pertactin gene. The only difference between the sequences of the oligonucleotides shown in FIGS. 6A and 6B is a single base change which generates the Apa I site. Plasmid S-4143-1 contains the FHAp/PRN hybrid gene inserted between the pertactin gene flanking regions for delivery to the PRN locus of a PRN deleted strains;

FIG. 6C shows the DNA sequence (SEQ ID NO: 5) of the oligonucleotides used to link the TOX promoter to the pertactin structural gene. The plasmids S-4140-1 and JB-811-2 contain the TOXp/PRN hybrid genes inserted between the pertactin gene flanking sequences. There is a single base difference between the two hybrid genes which introduces an Apa I site and changes one amino acid (Ala$^{12}$→Gly) of the pertactin signal sequence in S-4140-1. JB- 811-2 contains the TOXp/PRN hybrid gene encoding an authentic pertactin signal sequence;

FIGS. 7A, 7B, and 7C show the kinetics and expression of the 69 kDa protein from strains (A) 10536, (B) 1290-4 and (C) 591-473, with strains 1290-4 and 591-473 having the FHAp/PRN (A) and FHAp/PRN hybrid genes, respectively, at the PRN locus;

FIG. 8, comprising panels A, B and C, shows the genomic structure (panels A and B) and the Southern blot analysis (panel C) of restricted genomic DNA obtained from B. pertussis strains 10536 (wild type) and 390-59, which contains the FHAp/TOX hybrid at the TOX locus, and indicates that the hybrid operon was correctly placed;

FIG. 9, comprising panels A, B and C, shows the genomic structure (panels A, and B) and the Southern blot analysis (panel C) of strains 10536 and 890-49, which contains the TOXp/FHA hybrid at the FHA locus, and indicates that the hybrid operon was correctly placed;

FIG. 10, comprising panels A, B, C and D, shows the genomic structure (panels A, B and C) and the Southern blot analysis (panel D) of restricted genomic DNA from strains 10536, 1290-4 and 591-473. Southern blot analysis indicates the correct placement of the hybrid genes; and FIG. 11, comprising panels A, B, C and D, shows the genomic structure (panels A, B and C and the Southern blot analysis (panel D) of restricted genomic DNA from the wild-type strain 10536 and strains containing the TOXp/PRN hybrid genes. Strain 192-35 contains a modified pertactin signal sequence due to the addition of an Apa I site and strain 192-10 contains the authentic pertactin signal sequence. The hybrid genes were correctly placed at the PRN locus.

GENERAL DESCRIPTION OF INVENTION

Figure 3A:
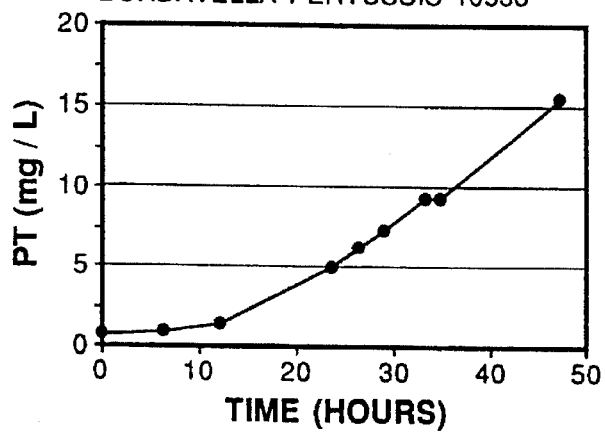
FIGS. 3A, 3B and 3C show the kinetics and expression levels of PT from strains (A) 10536, (B) 390-59, and (C) 590-11. Strain 390-59 contains the hybrid FHAp/TOX operon at the TOX locus while strain 590-11 contains the FHAp/TOX operon at the FHA locus plus the native TOX operon at the TOX locus.

*Bordetella pertussis* 10536 is the Connaught vaccine production strain of the assignee hereof and it has been used as the initial strain for all the work detailed by the inventors herein. The genes for PT, FHA, and pertactin have been cloned and sequenced (Nicosia et al., Proc. Natl. Acad. Sci., U.S.A., 83, 4631, [1986]; Loosmore et al., Nucl. Acids Res., 17, 8365, [1989]; Relman et al., Proc. Natl. Acad. Sci., U.S.A., 86, 2637, [1989]; Charles et al., Proc. Natl. Acad.

Sci., U.S.A., 86, 3554, [1989]).) and the promoter regions and transcriptional start of the structural genes have been determined. The inventors have generated hybrid genes by substituting the native promoters of a given gene by promoters from another gene of the organism. This was accomplished by fusing the promoters with the genes at the ATG start codon. Such fusions result in a native but autologous promoter, and a gene, if it encodes a secreted protein, with its natural signal sequence. In this specification, the term "autologous promoter" is used to denote a Bordetella promoter that is naturally associated with one Bordetella gene being transferred to transcribe a different Bordetella gene. The resultant hybrid genes then have been integrated at the appropriate gene loci in the chromosome of B. pertussis by homologous recombination.

As examples of the use of autologous promoters, genes have been created containing an FHA promoter with the TOX operon (FHAp/TOX), an FHA promoter with the PRN gene (FHAp/PRN), the TOX promoter with the FHA gene (TOXp/FHA), and the TOX promoter with the PRN gene (TOXp/PRN). A number of B. pertussis strains have been generated to demonstrate the efficacy of this strategy. In all cases, the autologous promoter functioned at its new location on the genome.

It was clearly demonstrated by this work that the promoter of one Bordetella gene may be replaced by that of another Bordetella gene, by inserting the FHAp/TOX hybrid at the TOX locus to generate B. pertussis strain 390-59. PT was secreted by this recombinant strain with kinetics and yields comparable to the wild-type strain 10536. (see FIG. 3B in comparison to normal kinetics of strain 10536 shown in FIG. 3A). The FHAp/TOX hybrid then was directed to the native FHA locus to generate B. pertussis strain 590-11 which now contains two copies of TOX. The yield and kinetics of PT production were consistent with the expression from two TOX genes, one directed by the FHA promoter in the hybrid operon, and the other from the native operon (see FIG. 3C). This experiment demonstrated that the FHAp/TOX hybrid gene may be integrated at and transcribed from two different loci in the genome.

PT holotoxin is an oligomeric protein composed of six subunits encoded by five different genes. In order to determine whether the FHA promoter can direct the expression of an increased amount of protein if the protein were not as structurally complex, strains were generated containing the FHAp/PRN (A) hybrid gene (B. pertussis strain 1290-4) and the FHAp/PRN hybrid gene (B. pertussis strain 591-473). The PRN gene encodes pertactin which is a Bordetella protein antigen consisting of a single 60 kD protein. Strain 591-473 contains the FHA promoter linked to the PRN structural gene through the authentic pertactin signal sequence. Strain 1290-4 contains the FHA promoter linked to the PRN structural gene through a modified pertactin signal sequence which has an Apa I restriction site in its DNA sequence. The yield of pertactin from strain 1290-4 was increased by three- to 10-fold in fermenters and shake flasks when its synthesis was directed by the FHA promoter (see FIG. 7B). The yield of pertactin from strain 591-473 was increased 10-fold in both fermentors and shake flasks (see FIG. 7C). Normal kinetics of pertactin production in a 10-litre fermenter are shown in FIG. 7A.

The overproduction of FHA can pose a problem in certain purification protocols. In order to reduce the yield of FHA to facilitate the purification of other antigens produced in lesser amounts, the native FHA promoter was substituted by the TOX promoter. The TOXp/FHA hybrid gene was directed to the FHA locus (i.e. B. pertussis strain 890-49) and the amount of FHA produced was significantly reduced, 50 to 100-fold (see FIG. 5B, with normal kinetics of FHA production shown in FIG. 5A).

Since the expression of PT from either its own TOX promoter or the FHA promoter in a hybrid FHAp/TOX gene was equivalent, hybrid genes containing the TOX promoter with the pertactin structural gene were generated. Pertactin expression levels from the strains harbouring these TOXp/PRN hybrid genes were equivalent to their FHAp/PRN counterparts.

The inventors have demonstrated by this work, as detailed in the Examples below, that it is possible to substitute promoters between Bordetella genes and obtain antigen production from the substituted promoters. It has been further demonstrated that it is possible to increase or decrease the yield of antigens in Bordetella pertussis by promoter replacement. The production of pertactin has been increased and that of FHA decreased. It is also possible that such a promoter replacement strategy may be used to alter the time-course as well as the yield of production of certain antigens. The regulation of protein production by this approach has broad application for fermentation and downstream processing technologies. Such a promoter replacement strategy can be used with any combination of genes in any genus of the species Bordetella.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, fermentation, protein biochemistry, and hybridoma technology used but not explicitly described in this disclosure and these Examples are amply reported in the scientific literature and are well within the ability of those skilled in the art. Further techniques of manipulation of B. pertussis are described U.S. Pat. No. 5,085,862, assigned to the assignee hereof and the disclosure of which is incorporated herein by reference.

All oligonucleotides were synthesized on an ABI model 380A DNA synthesizer and were purified by polyacrylamide gel electrophoresis. DNA manipulations were according to Sambrook et al. (Molecular cloning: a laboratory manual, second edition, Cold Spring Harbor Laboratory, Cold Spring Harbor, N.Y. [1989]). Restriction enzymes were used according to manufacturers' specifications. Site-directed mutagenesis was performed using the Amersham In Vitro Site-Directed Mutagenesis kit. The TOX, FHA and PRN genes were cloned from a lambda Charon 35 library containing Sau3A I fragments of Bordetella pertussis DNA from strain 10536. The structures of the chromosomal genes were confirmed by restriction mapping and partial or complete gene sequencing. Promoters of given genes were linked to the coding sequences of other genes using synthetic oligonucleotides. The correct fusions between the promoters and structural genes were confirmed either by manual dideoxy DNA sequencing (Sanger et al., Proc. Natl. Acad. Sci., U.S.A. 74, 5463, [1977]) or automated sequencing using an ABI model 370A DNA sequencer. Gene replacement in B. pertussis was achieved by homologous recombination following introduction of plasmid DNA into the cell by electroporation (Zealey et al., Bio/Technology, 8, 1025, [1990]). The TOX-deleted strain 29-8, FHA-deleted strain 390-101, and PRN-deleted strain 1090-108-3 were all prepared in a similar manner. In some instances, genes were integrated as non-replicating plasmids and allelic replacement achieved by growth of primary transformants under streptomycin selection (Stibitz et al., Gene, 50, 133, [1986], Zealey et al., Appl. Environ. Microbiol. 58, 208 [1992]). Chromosomal DNA was prepared as described by Yacoob and Zealey (Nucl. Acids Res. 16, 1639, [1988]) and Southern blot analysis performed according to Sambrook et al. using Gene Screen Plus (Dupont).

Deposit Information

Certain biological materials are described and referred to herein that have been deposited with the American Type Culture Collection (ATCC) located at 12301 Parklawn Drive Rockville, Md., 20852 U.S.A. pursuant to the Budapest Treaty and prior to the filing of this application and/or the filing of the prior application. Cultures of the deposited microorganisms will become available to the public upon grant of a patent based upon this United States patent application or the prior application, or publication of an equivalent application by the European Patent Office, as appropriate. The invention described and claimed herein is not to be limited in scope by the strains of microorganisms deposited, since the deposited embodiment is intended only as an illustration of the invention. Any equivalent microorganisms that produce equivalent changes in antigen production as described in this application are within the scope of the invention.

| | Deposit Summary | |
|---|---|---|
| Strain | ATCC Number | Deposit Date |
| 29-8 | 53973 | Nov 30 1989 |
| 390-101 | 55157 | Mar 6 1991 |
| 1090-108-3 | 55156 | Mar 6 1991 |
| 1290-4 | 55155 | Mar 6 1991 |
| 591-473 | 55321 | April 30 1992 |

Example 1

This Example illustrates the construction of the FHAp/TOX hybrid operon and its introduction into B. pertussis.

A pUC-based plasmid (S-3680-10) was constructed which contains the FHA promoter directing the expression of the native pertussis toxin structural gene and surrounded by the TOX flanking regions (FIG. 1). The FHA promoter is an EcoR I/Hinf I fragment of approximately 240 bp which includes any Bvg responsive elements (the TOX operon requires 170 bp for the Bvg responsive region). The complimentary oligonucleotides bridging the two gene sequences were annealed as an approximately 45 bp Hinf I/Ava I cassette which includes the start codon of the DNA segment coding for the leader sequence of PT subunit S1 (see FIG. 1). The remainder of the TOX operon from the Ava I site of the S1 gene to the EcoR I following the end of translation was used to complete the hybrid operon. The 3 kb Sma I/EcoR I 5'-flanking region and 4 kb EcoR I/Sal I 3'-flanking sequence of the native TOX locus were used to direct the hybrid operon to the TOX locus. (FIG. 1).

Figure 3B:
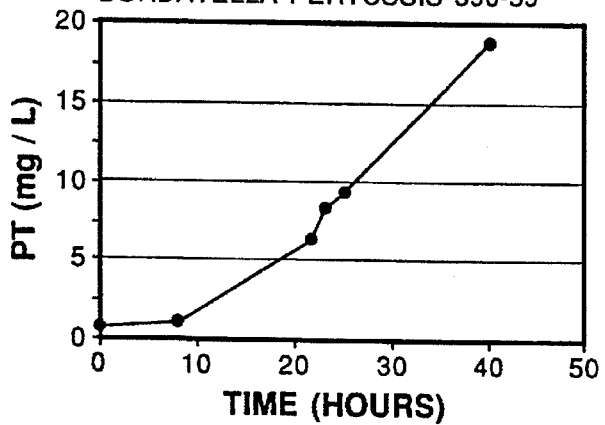
Figure 3C:
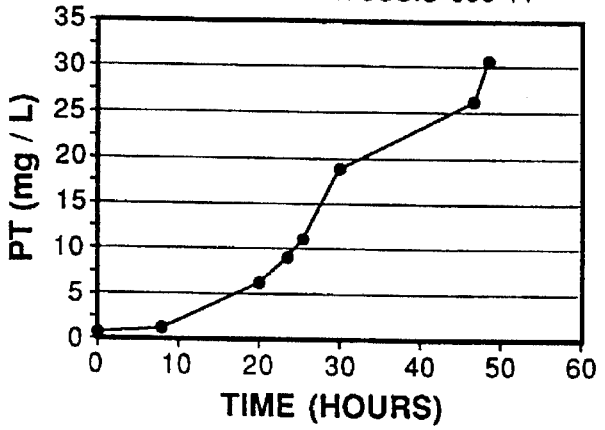

The FHAp/TOX hybrid plasmid was introduced into a TOX deleted derivative of B. pertussis 10536 (strain 29-8) by electroporation and this generated a strain (390-59) in which PT expression is directed by the FHA promoter. The kinetics and yield of PT expression from strain 390-59 were equivalent to those obtained with the parent strain 10536 (FIGS. 3A and 3B). The correct in situ integration of the FHAp/TOX hybrid operon at the TOX locus was demonstrated by restriction mapping and Southern blot analysis as shown in FIG. 8. The TOX deleted strain 29-8 has been deposited with the ATCC (accession number 53973) and is described in the aforementioned U.S. Pat. No. 5,085,862.

Example 2

This Example illustrates the construction of the FHAp/TOX hybrid operon and its introduction into an FHA-deleted strain of B. pertussis.

A pBR322-based plasmid (S-3749-18) was constructed which contains the FHA promoter fused to the structural genes for TOX at the start codon of the DNA segment coding for the S1 subunit leader sequence, surrounded by the FHA flanking regions. The hybrid operon was constructed as in Example 1. A 2.5 kb Bgl II/EcoR I 5'-flanking and a 1.7 kb EcoR I/Cla I 3'-flanking regions were used to direct the hybrid operon to the FHA locus (FIG. 2).

This FHAp/TOX hybrid plasmid was introduced into the FHA-deleted strain (390-101). This generated a strain (590-11) with two copies of TOX, one transcribed by its native promoter and one by the FHA promoter. The overall yield of PT was about twice that of strain 10536 and the kinetics of PT production were unchanged (see FIGS. 3A and 3B). The FHA-deleted strain 390-101 has been deposited with the ATCC on Mar. 6, 1991 (accession number ATCC 55157).

Example 3

This Example illustrates the construction of the TOXp/FHA hybrid gene and its introduction into B. pertussis.

A pBR322-based plasmid (S-3838-9) was constructed which contains approximately 500 bp of the TOX promoter region, starting at the EcoR I site. This sequence includes the Bvq responsive region at −170 bp. The 460 bp EcoR I/Nco I fragment of the TOX promoter is bridged to the FHA structural gene through an -100 bp Nco I/Sph I oligonucleotide (FIG. 4). The remainder of the FHA B structural gene from the Sph I site to the EcoR I site completed the hybrid operon. The 2.5 kb Bgl II/EcoR I FHA 5'-flanking and 1.7 kb EcoR I/Cla I 3'-flanking regions directed the hybrid operon to the FHA locus (FIG. 4). The correct integration of the TOXp/FHA hybrid operon at the FHA locus was demonstrated by Southern blot analysis as shown in FIG. 9.

Figure 5A:
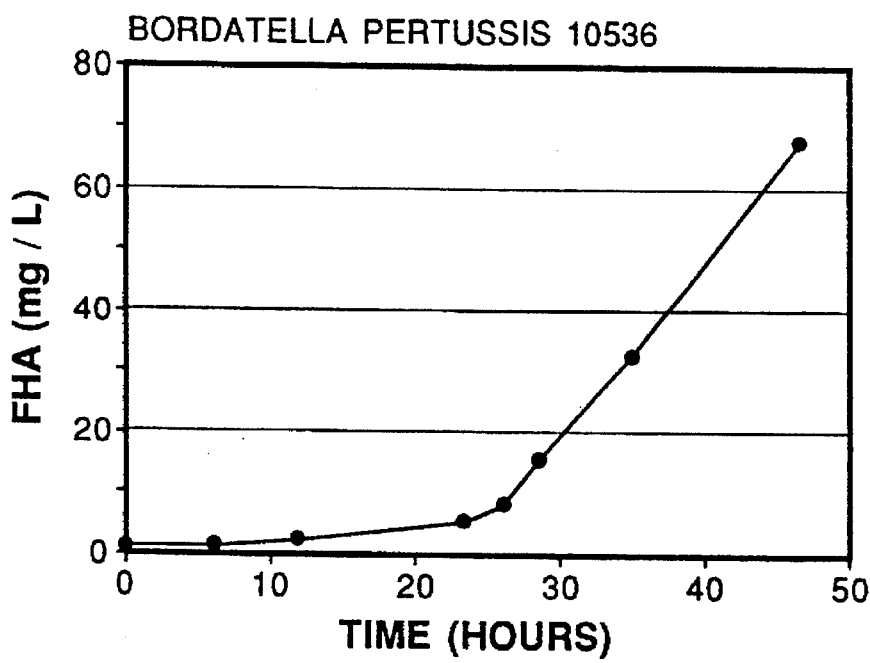
FIGS. 5A and 5B show the kinetics and expression of FHA from strains (A) 10536 and (B) 890-49 which contains the TOXp/FHA hybrid gene at the FHA locus.
Figure 5B:
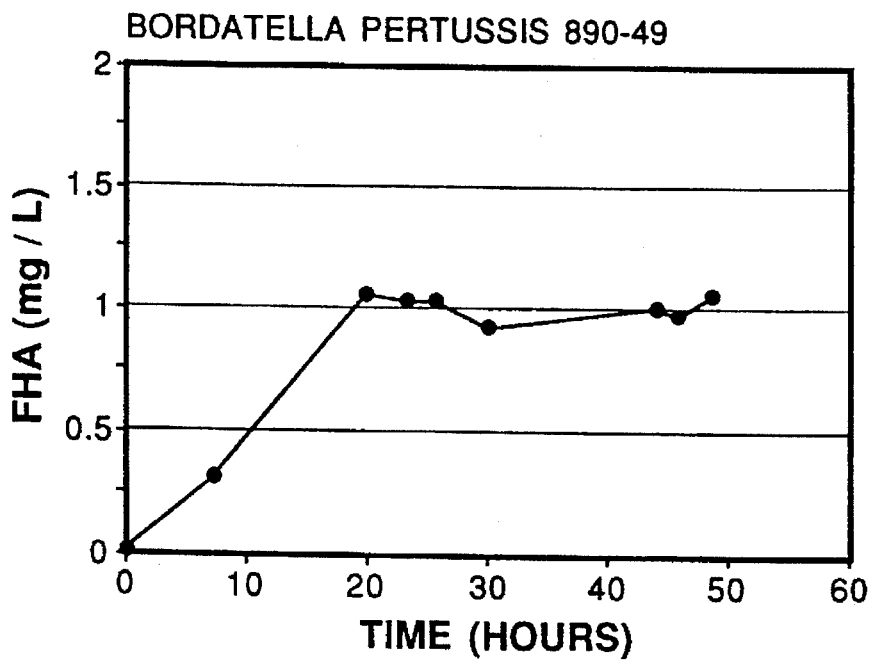

The strain (890-49) resulting from the chromosomal integration of the hybrid TOXp/FHA operon produced significantly reduced levels of FHA (FIGS. 5A and 5B).

Example 4

This Example illustrates the construction of the FHAp/PRN (A) hybrid gene and its introduction into B. pertussis.

The pUC-based plasmid S-3982-7 contains the FHA promoter fused at the start codon for the modified signal sequence of the pertactin structural gene and surrounded by PRN flanking sequences. The FHA promoter is an approximately 240 bp EcoR I/Hinf I fragment which is fused to the PRN structural gene through a 93 bp Hinf I/Nco I oligonucleotide (FIG. 6A). The oligonucleotides encode a modified pertactin signal sequence which has a single amino acid change, namely alanine 12 to glycine 12. The remainder of the pertactin structural gene from the Nco I site was added to complete the hybrid gene. The 1.6 kb Sau3A I/EcoR I 5'-flanking and 8 kb Apa I/Sau3A I 3'-flanking regions from PRN directed the hybrid gene to the PRN locus (see FIG. 6). The correct in situ placement of the FHAp/PRN hybrid gene at the PRN locus of the PRN deleted strain 1090-108-3 was demonstrated by restriction mapping and Southern blot analysis in FIG. 10.

Strain 1290-4 containing the FHAp/PRN (A) hybrid produced enhanced amounts of the pertactin outer membrane protein (see FIGS. 7A and 7B). The PRN deleted strain 1090-108-3 and strain 1290-4 have been deposited with the ATCC on Mar. 6, 1991 (accession numbers ATCC 55156 and ATCC 55155, respectively).

Example 5

This Example illustrates the construction of the FHAp/PRN hybrid gene and its introduction into *B. pertussis*.

The pUC-based plasmid S-4143-1 contains the FHA promoter fused at the start codon of the authentic signal sequence of the pertactin structural gene and surrounded by PRN flanking regions (see FIG. 6B). The FHA promoter is an approximately 240 bp EcoR I/Hinf I fragment which is fused to the PRN structural gene through a 93 bp Hinf I/Nco I oligonucleotide cassette encoding part of the natural pertactin signal sequence (FIG. 6B). The remainder of the pertactin structural gene from the Nco I site was added to complete the full-length hybrid gene. The 1.6 kb Sau3A I/EcoR I 5'-flanking and 8 kb Apa I/Sau3A I 3'-flanking regions from PRN directed the hybrid gene to the PRN locus. The correct in situ placement of the FHAp/PRN hybrid gene at the PRN locus of the PRN deleted strain 1090-108-3 is demonstrated by Southern blot analysis in FIG. 10.

Strain 591-473 containing the FHAp/PRN hybrid gene produced enhanced amounts of pertactin (FIG. 7C). *B. pertussis* strain 591-473 was deposited with the ATCC on Apr. 30 1992 and assigned the deposit number 55321.

Example 6

This Example illustrates the construction of the TOXp/PRN (A) hybrid gene and its introduction into *B. pertussis*.

The pUC-based plasmid S-4140-1 contains the TOX promoter fused at the start codon of a modified signal sequence of the pertactin structural gene and surrounded by the PRN flanking regions (FIG. 6C). An approximately 500 bp EcoR I/Kpn I DNA fragment containing the TOX promoter with its Bvq-responsive element was fused to the PRN structural gene through a 123 bp Kpn I/Apa I oligonucleotide cassette. The Apa I site was introduced for construction purposes and resulted in a single amino acid change (Ala$^{12}$→Gly) in the pertactin signal sequence as described in Example 4 above. The remainder of the PRN structural gene from the Apa I site was added to complete the hybrid gene. The hybrid gene was inserted between the PRN flanking regions as described in Examples 4 and 5 above to generate plasmid S-4140-1. The correct in situ placement of the hybrid gene at the PRN locus of the PRN deleted strain 1090-108-3 was demonstrated by Southern blot analysis of the resultant strain 192-35 (FIG. 11). Strain 192-35 containing the TOXp/PRN (A) hybrid gene produced enhanced amounts of pertactin (Table 1).

Example 7

This Example illustrates the modification of the TOXp/PRN (A) hybrid gene by site-directed mutagenesis to generate an authentic pertactin signal sequence and the introduction of the TOXp/PRN hybrid gene into *B. pertussis*.

Plasmid S-4140-1 contains the TOXp/PRN (A) hybrid gene which encodes a modified pertactin signal sequence. The Kpn I fragment was subcloned into M13mp18 and subjected to site-directed mutagenesis in order to generate an authentic coding sequence for the pertactin signal sequence by removing the Apa I site. Restoration of the native DNA sequence was confirmed by DNA sequencing. When the mutated (native sequence) Kpn I fragment was cloned back into S-4140-1, plasmid JB-811-2 was generated which contains a TOXp/PRN hybrid gene encoding an authentic pertactin signal sequence. The correct in situ placement of the TOXp/PRN gene at the PRN locus of strain 1090-108-3 to generate strain 192-10 was demonstrated by restriction mapping and Southern blot analysis (FIG. 11).

When strain 192-10 was grown in liquid culture, it produced enhanced amounts of pertactin relative to the wild-type strain and strain 192-35 (Table 1).

Example 8

This Example illustrates the preparation of *B. pertussis* strains containing hybrid operons and their structural analysis.

Strains deleted for TOX (29-8), FHA (390-101), or PRN (1090-108-3) were engineered using homologous recombination between the Connaught vaccine strain 10536 and plasmid DNA containing flanking regions of the desired genes, as described by Zealey et al. (Bio/Technology 8, 1025, [1990]). The flanking regions used for deleting and replacing genes were as described in Examples 1, 2, 3 and 4. The flanking regions surrounded a cassette containing a tetracycline resistance gene and an *E. coli* S12 gene which was inserted at the locus for the deleted structural genes. During another round of allelic exchange, this cassette was subsequently replaced by the hybrid genes.

To confirm correct in situ placement of the hybrid genes, restriction digests and Southern blot analyses were performed on genomic DNA purified from the recombinant strains.

Example 9

This Example illustrates the preparation of Southern blots for the *B. pertussis* strain 390-59 (see FIG. 8).

Chromosomal DNA was isolated from wild-type (WT) *B. pertussis* 10536 (lanes 1–2) and *B. pertussis* 390-59 (lanes 3–4), restricted with the endonucleases Kpn I/Sma I (lanes 1 and 3) and Bgl II (lanes 2 and 4) and probed with a 4.7 kb EcoR I restriction fragment that represents the entire TOX coding sequence. Replacement of the TOX promoter by the FHA promoter resulted in the loss of a KpnI site as shown by the arrow in FIG. 8. Digestion with KpnI and SmaI produced TOX-specific hybridization fragments of 5.1, 3.0 and 1.6 kb for *B. pertussis* 10536 and 4.8 and 5.1 kb for *B. pertussis* 390-59.

Example 10

This Example illustrates the preparation of a Southern blot for *B. pertussis* strain 890-49 (FIG. 9).

Chromosomal DNA was isolated from wild-type (WT) *B. pertussis* 10536 (lanes 1–2) and *B. pertussis* 890-49 (lanes 3–4), restricted with the endonucleases Kpn I/Bgl II (lanes 1 and 3) and Bam HI (lanes 2 and 4) and probed with an FHA specific probe. Replacement of the FHA promoter by the TOX promoter resulted in the introduction of a Kpn I site as shown in FIG. 9. Digestion with Kpn I and Bgl II produced FHA-specific hybridization fragments of 9 kb for *B. pertussis* 10536 and 6.6 kb for *B. pertussis* 890-49.

Example 11

This Example illustrates the preparation of a Southern blot for *B. pertussis* strains 1290-4 and 591-473 (see FIG. 10).

Chromosomal DNA was isolated from wild-type (WT) *B. pertussis* 10536 (lanes 1, 3 and 5) and *B. pertussis* 1290-4 (lanes 2 and 7), and *B. pertussis* 591-473 (lanes 4 and 8), restricted with the endonucleases Apa I (lanes 1 and 2) Dde I (lanes 3 and 4) and Sal I (lanes 5 to 8), and probed with a PRN specific probe. Lane 6 contains the PRN-deleted strain 1090-108-3. The modification of the signal sequence in strain 1290-4 resulted in the introduction of an ApaI site which produced PRN-specific hybridization fragments of 7.0 kb for *B. pertussis* 10536 and 2.5 kb for *B. pertussis* 1290-4 as shown in FIG. 10 (lanes 1 and 2 respectively). The FHA promoter also has a Dde I site which is not present in the PRN promoter. The appearance of the 1.6 kb band for strain 591-473 in lane 4 indicates the presence of the FHA promoter.

Example 12

This Example illustrates the preparation of a Southern blot for *B. pertussis* strains 192-10 and 192-35 (FIG. 11).

Chromosomal DNA was isolated from wild-type *B. pertussis* 10536 (lanes 1, 4 and 7), 192-10 (lanes 2, 5 and 8), and 192-35 (lanes 3, 6 and 9), restricted with Apa I (lanes 1 to 3), Kpn I (lanes 4 to 6), and Sal I (lanes 7 to 9), and probed with a PRN-specific probe. Replacement of the PRN promoter with the TOX promoter resulted in the introduction of a Kpn I site in 192-10 and 192-35, as well as an extra Apa I site in 192-35. The introduction of the Kpn I site produced hybridization fragments of 8 kb (lane 4, wild-type) and 1.6 kb (lanes 5 and 6, hybrids). The additional Apa I site in strain 192-35 resulted in a PRN-specific hybridization fragment of 2.5 kb (lane 3).

Example 13

This Example illustrates the growth of *B. pertussis* strains and immunoassays for the quantification of specific antigens.

*Bordetella pertussis* strains were grown in modified Stainer-Scholte medium containing 0.2% heptakis (2,6-0-dimethyl) β-cyclodextrin (Imaizumi et al, Infect. Immun. 41, 1138, [1983]) either in 10 liter CHEMAP (trade-mark fermenters, controlled for pH and dissolved oxygen, or in 10 ml culture. Culture supernatants were tested for antigen production in antigen-specific ELISAs. PT was measured in a fetuin-capture ELISA as described in Loosmore et al. (Infect. and Immun. 58, 3653, [1990]). FHA was captured by a mouse monoclonal anti-FHA antibody purified from ascites fluid and the second antibody was a polyclonal rabbit IgG anti-FHA conjugated to horse-radish peroxidase. Pertactin was captured with a polyclonal antibody purified from a monospecific guinea pig hyperimmune serum and the second antibody was a guinea pig IgG anti-69 kDa conjugated to horse-radish peroxidase. PT, FHA and 69 kDa proteins purified from fermentation broths of the wild-type production strain 10536 were used as standards.

SUMMARY OF DISCLOSURE

In summary of this disclosure, the present invention provides a novel means of gene product expression having application to Bordetella species, particularly *Bordetella pertussis*. Modifications are possible within the scope of this invention.

TABLE 1

Production of pertussis toxin (PT), filamentous hemagglutinin (FHA) and pertactin, from *Bordetella pertussis* strains that contain hybrid prn alleles at the prn locus. The strains were grown in 10 ml shake-flasks and antigen levels in culture supernantants determined by antigen-specific ELISAs.

| | | Antigen Expression (μg ml⁻¹)* | | |
|---|---|---|---|---|
| Strain | Construction | PT | FHA | Pertactin |
| 10536 | wild-type | 5.9 | 53.7 | 8.9 |
| 1090-108-3 | prn Δ | 1.6 | 31.9 | 0 |
| 1290-4 | fha (ApaI) | 4.2 | 44.7 | 30 |
| 591-473 | fha | 4.2 | 47.9 | 73.6 |
| 192-10 | toxp | 4.8 | 45.3 | 42.5 |
| 192-35 | toxp (ApaI) | 4.5 | 50.6 | 19.2 |

| SEQUENCE IDENTIFICATIONS | | |
|---|---|---|
| Sequence No. | Identification | Figure |
| ID NO: 1 | Oligonucleotide linker: FHAp/TOX hybrid gene | 1 |
| ID NO: 2 | Oligonucleotide linker: TOXp/FHA hybrid gene | 4 |
| ID NO: 3 | Oligonucleotide linker: FHAp (A) PRN hybrid gene | 6A |
| ID NO: 4 | Oligonucleotide linker: FHAp/PRN hybrid gene | 6B |
| ID NO: 5 | Oligonucleotide linker: TOXp/PRN hybrid gene | 6C |

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 91 base pairs
( B ) TYPE: nucleic acid
( C ) STRANDEDNESS: single (D) TOPOLOGY: linear (ii) MOLECULE TYPE: DNA (genomic)

(ix) FEATURE:
    (A) NAME/KEY: intron
    (B) LOCATION: 1..45

(xi) SEQUENCE DESCRIPTION: SEQ ID NO:1:

| | | | | | | |
|---|---|---|---|---|---|---|
| ATTCTGCCGA | TTACTTCACT | TCGCTGGTCG | GAATATGCGT | TGCACGACGG | CTAATGAAGT | 60 |
| GAAGCGACCA | GCCTTATACG | CAACGTGAGC | C | | | 91 |

(2) INFORMATION FOR SEQ ID NO:2:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| CATGGTGTGA | TCCGTAAAAT | AGGCACCATC | AAAACGCAGA | GGGGAACACA | CTAGGCATTT | 60 |
| TATCCGTGGT | AGTTTTGCGT | CTCCCCTTGA | CGGGATGAAC | ACGAACCTGT | ACAGGCTGGT | 120 |
| CTTCAGCCAT | GTTCGCGGCA | TGCTGCCCTA | CTTGTGCTTG | GACATGTCCG | ACCAGAAGTC | 180 |
| GGTACAAGCG | CC | | | | | 192 |

(2) INFORMATION FOR SEQ ID NO:3:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| ATTCTGCCGA | TTACTTCACT | TCGCTGGTCG | GAATATGAAC | ATGTCTCTGT | CACGCGACGG | 60 |
| CTAATGAACT | GAAGCGACCA | GCCTTATACT | TGTACAGAGA | CAGTGCGATT | GTCAAGGCGG | 120 |
| GGCCCCTGCG | CCGCACCACG | CTGGCTAACA | GTTCCGCCCC | GGGGACGCGG | CGTGGTGCGA | 180 |
| CCGGTAC | | | | | | 187 |

(2) INFORMATION FOR SEQ ID NO:4:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| | | | | | | |
|---|---|---|---|---|---|---|
| ATTCTGCCGA | TTACTTCACT | TCGCTGGTCG | GAATATGAAC | ATGTCTCTGT | CACGCGACGG | 60 |
| CTAATGAACT | GAAGCGACCA | GCCTTATACT | TGTACAGAGA | CAGTGCGATT | GTCAAGGCGG | 120 |
| CGCCCCTGCG | CCGCACCACG | CTGGCTAACA | GTTCCGCCGC | GGGGACGCGG | CGTGGTGCGA | 180 |
| CCGGTAC | | | | | | 187 |

(2) INFORMATION FOR SEQ ID NO:5:

( i ) SEQUENCE CHARACTERISTICS:
  ( A ) LENGTH: 246 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| CGGTCACCGT | CCGGACCGTG | CTGACCCCCC | TGCCATGGTG | TGATCCGTAA | AATAGGCACC | 60
| ATCAAAACGC | CATGGCCAGT | GGCAGGCCTG | GCACGACTGG | GGGGACGGTA | CCACACTAGG | 120
| CATTTTATCC | GTGGTAGTTT | TGCGAGAGGG | GAAGACGGGA | TGAACATGTC | TCTGTCACGC | 180
| ATTGTCAAGG | CGGGGCCTCT | CCCCTTCTGC | CCTACTTGTA | CAGAGACAGT | GCGTAACAGT | 240
| TCCGCC | | | | | | 246

What we claim is:

1. A hybrid Bordetella gene comprising a Bordetella gene fused at the ATG start codon to an autologous Bordetella promoter, wherein:
   (a) said promoter is the pertussis toxin operon (TOXp) promoter and the Bordetella gene is selected from the group consisting of the filamentous haemagglutinin operon (FHA) and pertactin (PRN) gene; or
   (b) said promoter is the filamentous haemagglutinin operon (FHAp) promoter and the Bordetella gene is selected from the group consisting of pertussis toxin operon (TOX) and pertactin (PRN) gene.

2. The hybrid gene of claim 1 wherein said TOXp and FHAp promoters are of *Bordetella pertussis* and the TOX, FHA, end PRN genes are of *Bordetella pertussis*.

3. A viable strain of Bordetella containing a hybrid Bordetella gene comprising a Bordetella gene fused at an ATG start codon to an autologous Bordetella promoter or a multiple of said hybrid gene, wherein said viable strain of Bordetella produces, upon culture, a gene product at a yield of production which is altered from the yield of production achieved by a Bordetella strain containing a Bordetella gene fused at an ATG start codon to its own native Bordetella promoter, wherein:
   (a) said autologous promoter is the pertussis toxin operon (TOXp) promoter and the Bordetella gene is selected from the group consisting of the filamentous haemagglutinin operon (FHA) and pertactin (PRN) gene, or
   (b) said autologous promoter is the filamentous haemagglutinin operon (FHA) promoter and the Bordetella gene is selected from the group consisting of the pertussis toxin operon (TOX) and pertactin (PRN) gene.

4. The viable strain of claim 3 wherein said TOXp and FHAp promoters are of *Bordetella pertussis* and the TOX, FHA, and PRN genes are of *Bordetella Pertussis*.

5. The viable of claim 3 wherein the strain of Bordetella containing said hybrid Bordetella gene is *Bordetella pertussis*.

6. The viable strain of claim 4 which is the FHAp/PRN (A) transformed strain of *B. pertussis* No. 1290-4, as deposited with ATCC under accession No. 55155.

7. The viable strain of claim 4 which is the FHAp/PRN transformed strain of *B. pertussis* No. 591- 473, as deposited with ATCC under accession No. 55321.

8. A plasmid, which comprises a hybrid Bordetella gene as claimed in claim 1.

9. A plasmid which is plasmid S-3982-7 having the restriction map shown in FIG. 6A.

10. A plasmid which is plasmid S-4143-1 having the restriction map shown in FIG. 6B.

11. A whole-cell vaccine against the disease of whooping cough, comprising an immunoprotective amount of a killed form of at least one strain of Bordetella containing a hybrid Bordetella gene as claimed in claim 3 and a physiologically-acceptable carrier therefor.

12. A method of expression of a gene product from a Bordetella strain which comprises:
   (a) forming a hybrid Bordetella gene comprising a Bordetella gene fused at the ATG start codon to an autologous Bordetella promoter, wherein:
      (1) said promoter is the pertussis toxin operon (TOXp) promoter and the Bordetella gene is selected from the group consisting of the filamentous haemagglutinin operon (FHA) and pertactin (PRN) gene; or
      (2) said promoter is the filamentous haemagglutinin operon (FHAp) promoter and the Bordetella gene is selected from the group consisting of pertussis toxin operon (TOX) and pertactin (PRN) gene;
   (b) introducing said hybrid gene into a Bordetella strain to form a viable transformed Bordetella strain; and
   (c) culturing said transformed Bordetella strain to effect expression of a gene product encoded by said hybrid gene at a production yield which is different from the production yield achieved when said Bordetella strain contains a Bordetella gene fused at an ATG start codon to its own native promoter.

13. The method of claim 12 wherein introduction of said hybrid gene is carried out by AC Aug. 31, 1996 integrating said hybrid gene in the chromosome of said Bordetella strain by homologous recombination.

14. The method of claim 12 wherein said Bordetella strain is *Bordetella pertussis*.

* * * * *